(12) United States Patent
Bridges et al.

(10) Patent No.: US 6,904,801 B1
(45) Date of Patent: Jun. 14, 2005

(54) FUNCTIONAL CAPACITY EVALUATION APPARATUS AND METHOD

(76) Inventors: Tony Bridges, 9042 Sturbridge Pl., Montgomery, AL (US) 36116; Steven F. Windham, 8648 Old Savannah La., Montgomery, AL (US) 36116

(*) Notice: Subject to any disclaimer, the term of this patent is extended or adjusted under 35 U.S.C. 154(b) by 175 days.

(21) Appl. No.: 10/134,884

(22) Filed: Apr. 29, 2002

(51) Int. Cl.$^7$ .................................................. A61B 5/22
(52) U.S. Cl. ................................................. 73/379.01
(58) Field of Search ........................ 73/379.01, 379.02, 73/379.03, 379.04

(56) References Cited

U.S. PATENT DOCUMENTS

| | | | |
|---|---|---|---|
| 5,142,910 A | | 9/1992 | Litchman |
| 5,260,870 A | * | 11/1993 | Tsuchiya et al. ............ 600/595 |
| 5,271,416 A | | 12/1993 | Lepley |
| 5,275,045 A | * | 1/1994 | Johnston et al. ......... 73/379.01 |
| 5,348,519 A | * | 9/1994 | Prince et al. .................. 482/6 |
| 5,437,587 A | | 8/1995 | Prince et al. |
| 5,456,648 A | | 10/1995 | Edinburg et al. |
| 5,891,042 A | | 4/1999 | Sham et al. |
| 6,056,671 A | | 5/2000 | Marmer |
| 6,086,517 A | | 7/2000 | Schapmire |
| 6,216,535 B1 | | 4/2001 | Schapmire |
| 6,227,047 B1 | | 5/2001 | Livingston |
| 6,672,157 B2 | * | 1/2004 | MacFarlane et al. ..... 73/379.01 |

* cited by examiner

*Primary Examiner*—Edward Lefkowitz
*Assistant Examiner*—Jewel Thompson
(74) *Attorney, Agent, or Firm*—Smith, Gambrell & Russell, LLP

(57) ABSTRACT

An apparatus and method is provided for testing the ability of an individual to lift objects under various conditions. During standard lifting tests, the average acceleration and velocity of each lift, as well as the distribution of force between the hands and feet of the patient, are electronically measured and recorded. These objective factors can then be used to determine whether the patient is exerting maximal effort, and to assess a patient's condition and progress during a rehabilitation program.

20 Claims, 3 Drawing Sheets

FUNCTIONAL CAPACITY EVALUATION APPARATUS AND METHOD

FIELD OF THE INVENTION

This invention is related to the field of human functional capacity testing. In particular, the invention provides an apparatus and method for testing the ability of an individual to lift objects under various conditions, and for objectively determining whether the individual is exerting maximal effort during such tests.

BACKGROUND OF THE INVENTION

In the field of physical medicine and rehabilitation, various professionals are often called upon to assess the functional capacity of a patient. Functional Capacity Evaluations ("FCEs") are used extensively throughout the United States to ascertain an individual's status in regards to the extent of a disability and/or the ability to return to work. FCEs have assumed particular importance in light of the high cost of worker's compensation claims for industrial accidents.

The ability to lift is one of the critical factors affecting a patient's ability to return to work. Thus one of the most important functions of an FCE is determining the patient's ability to lift particular amounts of weight in particular configurations, including floor to shoulder, floor to waist, knuckle to shoulder, and shoulder to overhead. The question with such tests, however, is always whether the patient has given maximal effort, so that the results of the test present a true picture of the patient's functional capabilities.

At present, there is no system which can accurately determine whether a patient has given maximal effort. While indicators such as mechanical breakdown, postural breakdown, recruitment of accessory muscles, and heart rate may be used, the application of these indicators is to some degree subjective and thus subject to question. Furthermore, many evaluators administering FCE's may have inadequate experience to determine whether true maximal effort was given.

While patients have been known to manipulate FCE results by conscious and unconscious efforts, there are certain variables that cannot be manipulated. In particular, as maximal effort and maximal weights are achieved, the expected outcome is slower time to complete the lift, along with decreased velocity and acceleration.

The most widely given reason for inability to lift additional weight is pain. Pain has been shown to result in decreased range and velocity of motion for affected body segments. It is also well known that when pain is present it affects the strength of muscular contraction. Therefore, if pain is truly present in a given lift, the variables of speed, velocity, and acceleration will be adversely affected. Test results which are inconsistent with these expectations (for example where velocity and acceleration does not decrease significantly between a previous lift and a lift with greater weight claimed to represent "maximal effort," or where the velocity and acceleration for two lifts of the same weight during different portions of an FCE vary dramatically) may indicate that the patient is not expending maximal effort, or is otherwise attempting to manipulate the test results.

The force distribution between the patient's legs when performing lifts is another objective factor which can be taken into account in assessing functional capacity, particularly for patients who claim either lower back or lower extremity pathology. Many patients with spinal disc pathology have symptoms related to one of the lower extremities, which may impair strength and sensation as well as functional status (e.g. the ability to squat, kneel, climb stairs, lift, etc.). Patients manipulating the system may consciously walk with an antalgic gait and shift their weight more to one side when standing, but during a lift will often unconsciously apply force symmetrically on both legs, thereby illustrating their actual functional status with respect to the allegedly "weak" leg. Measuring force distribution during lifting may also give a physician or rehabilitation professional valuable information regarding the patient's diagnosis and progress during a rehabilitation program.

Likewise, the force distribution between the patient's hands during a lift may shed light on the true condition of patients complaining of pain or weakness in one arm due to upper back pathology or other causes. Further information regarding the relative strength of each arm may also be gathered by utilizing a program of one-armed lifts and collecting information on the velocity, acceleration, and force generated.

Several devices have previously been developed to measure these and other objective indicators during FCEs. For example, Marmer's "Functional capacity assessment system and method", U.S. Pat. No. 6,056,671, uses digitized video to determine the velocity and acceleration of lifts during a functional capacity evaluation. However, this system makes use of multiple video cameras and a computer system, as well as visual indicators which have to be applied to the patient. Accordingly, the system may be somewhat complex and expensive, and requires substantial time to set up and operate, rendering it unsatisfactory for some FCE applications. Additionally, it provides no mechanism for measuring force distributions between the patient's hands and feet.

Lepley's "Exercise platform for physiological testing," U.S. Pat. No. 5,271,416, also can be used to collect lift velocity and acceleration information, as well as data regarding the force applied by the patient's feet (though not hands) during a lift. However, this system uses a cable spool with a handle to simulate the lifting of an object, and so may not accurately reproduce the circumstances encountered in a "real world" lift, which is a primary goal in the development of FCE test protocols.

Accordingly, it would be advantageous to have a system for use in FCE testing which could accurately collect velocity, acceleration, and force distribution data in a test format which is already familiar to FCE evaluators and closely mimics actual dynamic lifting conditions, while being relatively inexpensive to manufacture, and easy to set up and operate.

SUMMARY OF THE INVENTION

It is the primary object of the present invention to provide an apparatus and method for testing the ability of an individual to lift objects under various conditions, and for objectively determining whether the patient is exerting maximal effort during the tests. In the method and apparatus disclosed herein, standard lifting tests are conducted in a manner well known in the art. The average acceleration and velocity of each lift, as well as the distribution of force between the hands and feet of the patient, is electronically measured and recordes. These objective factors can then be used to determine whether the patient is exerting maximal effort

DESCRIPTION OF THE PREFERRED EMBODIMENTS

Figure 1:
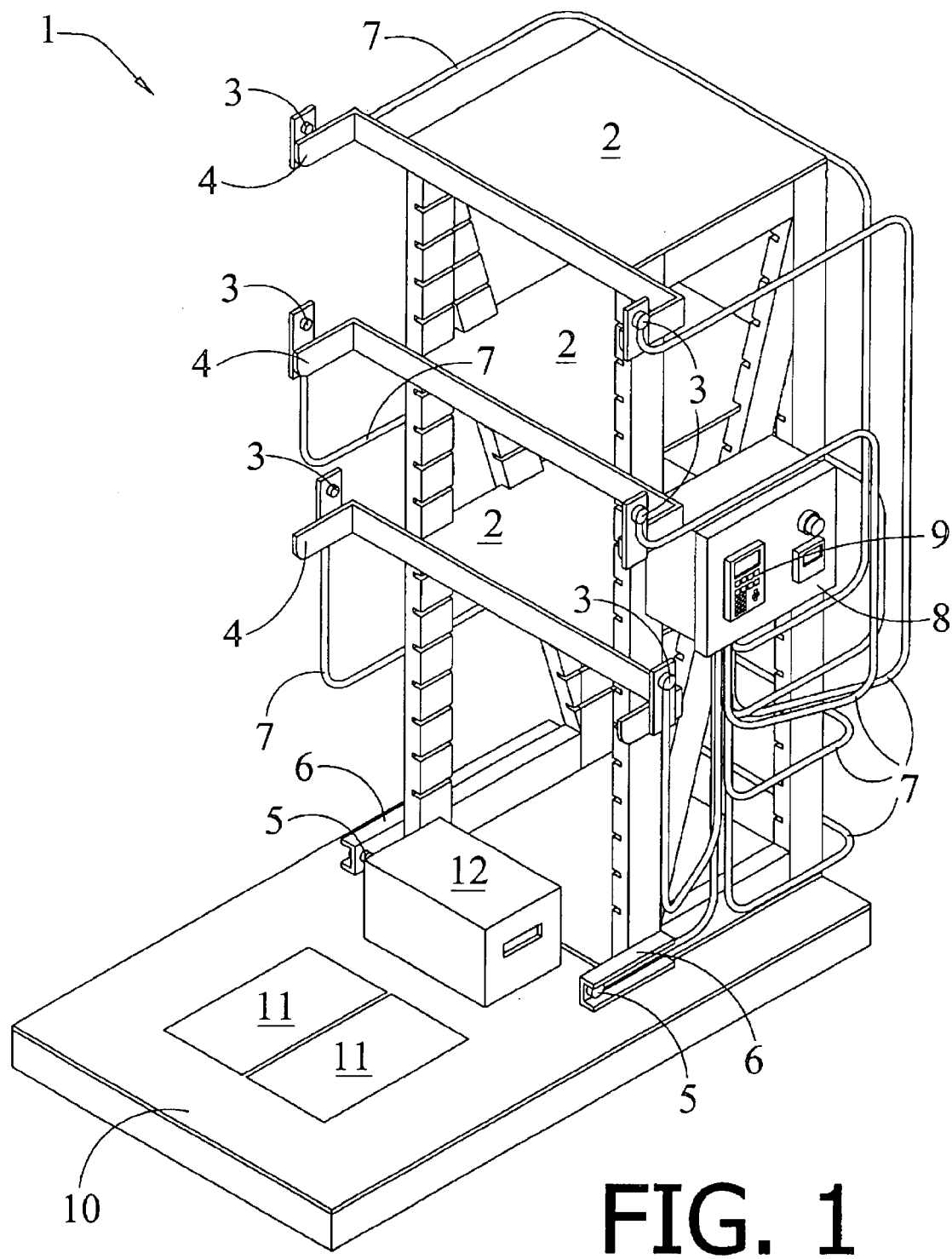
FIG. 1 is a perspective view of a preferred embodiment of the present invention.
Figure 2:
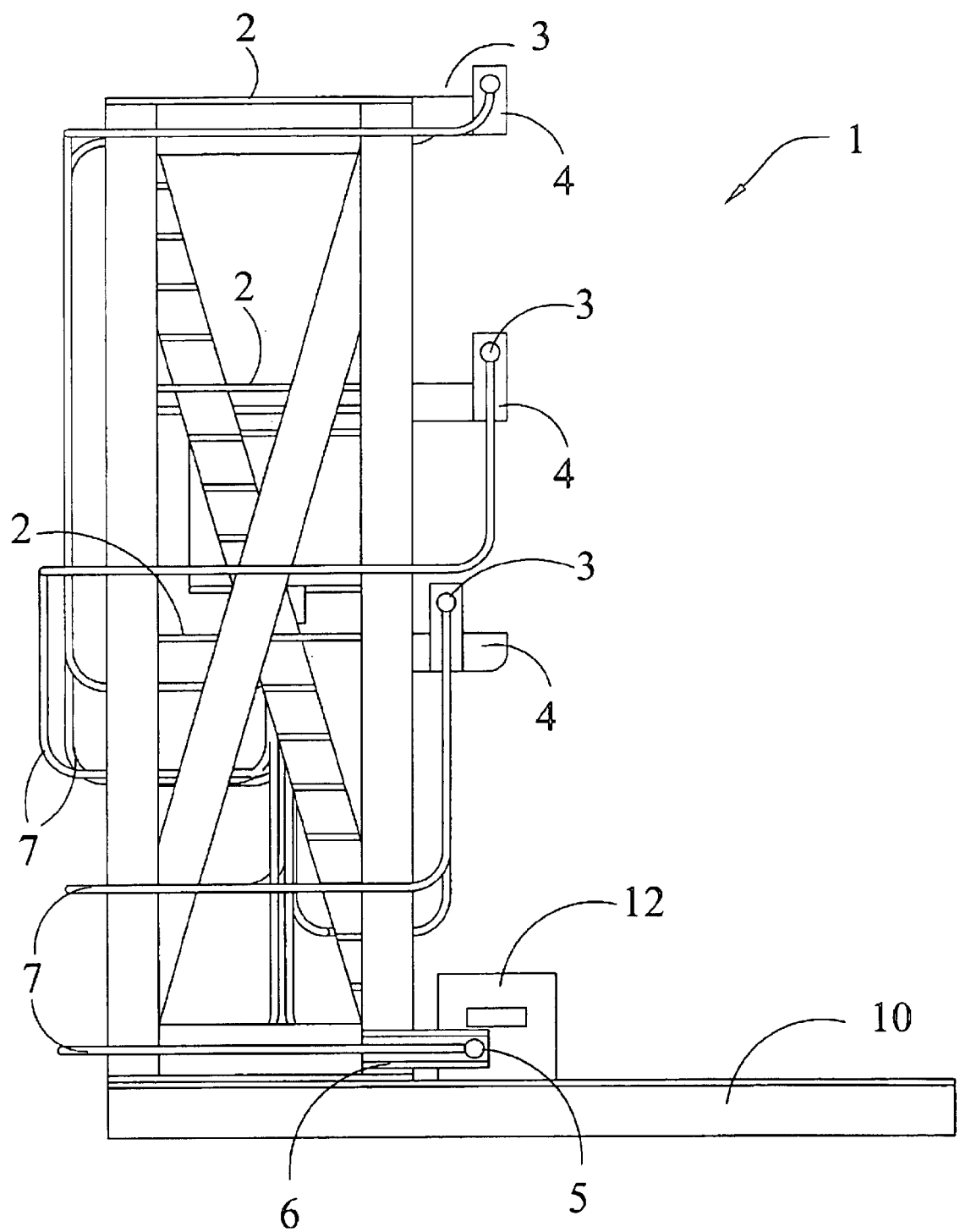
FIG. 2 is a side view illustrating the opposite side of the same preferred embodiment.
Figure 3:
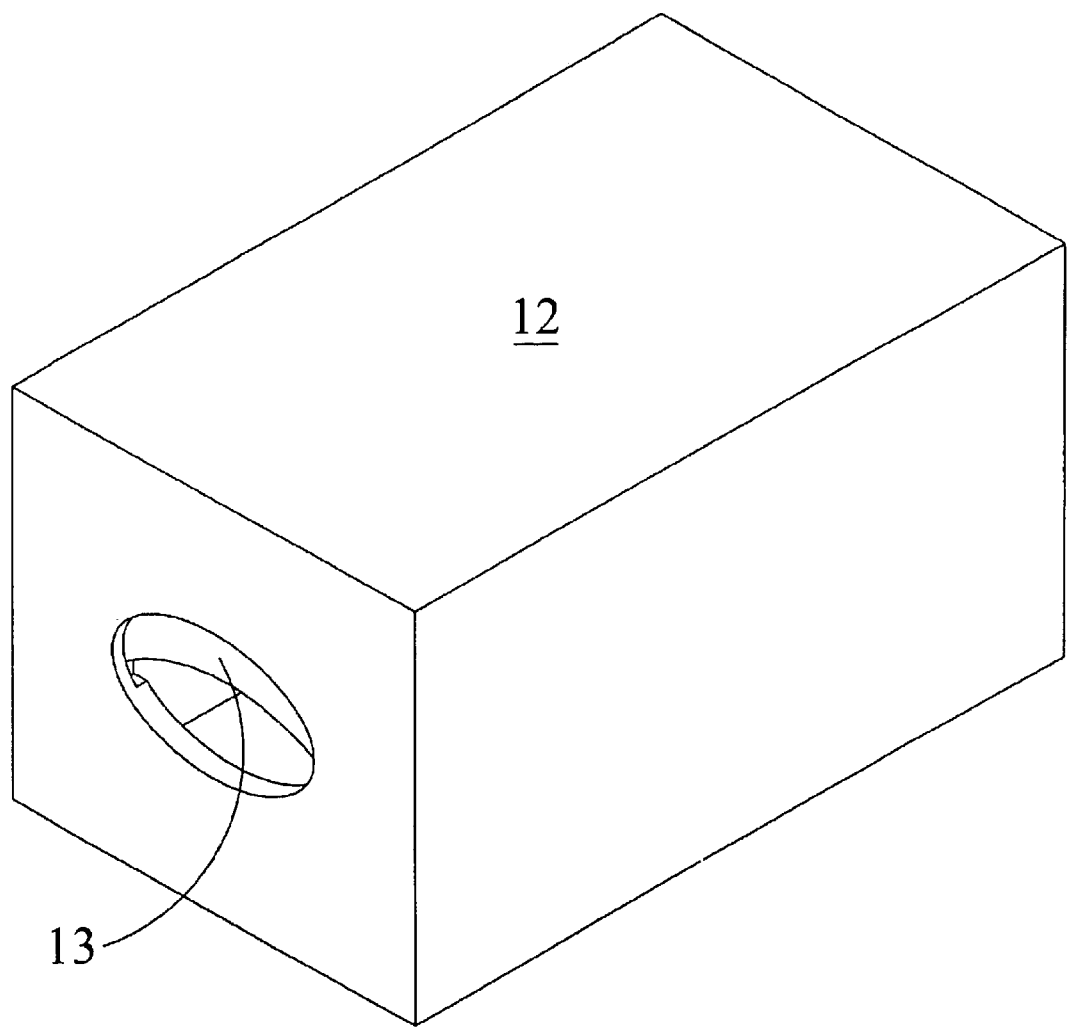
FIG. 3 is a perspective view of a weighted box equipped with pressure sensors for use in conjunction with the present invention.

FIGS. 1 and 2 illustrate a preferred embodiment of the subject invention. In this embodiment, a rack 1, of a type in common use in the FCE industry, provides support for a shelf or shelves 2. The rack is constructed so as to permit the height of the shelf or shelves to be adjusted, preferably up to at least 76 inches off the ground. Sensors 3 (which may utilize infrared, laser, photoelectric, or other technologies) are affixed to supports 4 at the front of each shelf, and detect the motion of objects passing in front of the shelf. Similar sensors 5 are also attached to supports 6 affixed to the base of the rack 1. In one preferred embodiment, the sensors 3 and 5 are transmitted beam photoelectric sensors (Allen-Bradley).

The sensors 3 and 5 are connected via cables 7 to a microprocessor control system (e.g. Allen-Bradley Micrologix 1200) (not shown) located within a control box 8. The microprocessor control system is in turn connected to an operator interface 9 (e.g. Allen-Bradley Panelview 300), which includes a manual override button, affixed to the front of the control box 8.

At the base of the rack 1 is a platform 10 which contains apertures for two foot plates 11. Load cells (Hardy Instruments) (not shown) measure the force applied to each plate. These load cells are connected via cables (not shown) to the microprocessor control system.

Additionally the object being lifted 12 can be equipped with sensors for determining the amount of force being applied by each of the patient's hands. In one preferred embodiment, pressure plates 13 can be affixed within apertures in the sides of the box. Load cells (not shown) measure the force applied to each plate. These load cells are connected via cables (not shown) to the microprocessor control system. In alternative embodiments, the box or other object being lifted could be fitted with handles equipped with sensors to measure the force being exerted on them, or the patient could wear gloves similarly equipped with force sensors.

When the invention is in use, the patient stands on the foot plates 11 and lifts a box 12 or other weighted object from the base of the rack (as shown in FIG. 1) to a shelf, or from a lower shelf to a higher shelf. As is well known in the art, additional weights may be added to the inside of the box 12, and the shelves adjusted to present any of a wide range of lifting conditions, including floor to overhead, floor to shoulder, floor to waist, knuckle to shoulder, and shoulder to overhead lifts. A variety of established FCE testing protocols may be used with the invention.

The operator first enters the distance of the lift into the operator interface 9 and then activates the system. The sensors 3 and 5 measure the time when the box 12 leaves the vicinity of the base of the rack or lower shelf and when it passes in front of the higher shelf. (If, due to the individual patient's lift mechanics or other factors, the sensors are not accurately capturing the initiation or termination of the lift, the manual override may be used.) Simultaneously, the load cells measure the force applied to each plate 11 and 13 during the duration of the lift. The microprocessor control system then calculates the time required to complete the lift, the average velocity and acceleration of the lift, and the average force applied by each of the patient's hands and feet during the lift.

This information is available for display to the operator on the operator interface's display screen. The operator can record this information (either on paper or in a digital format) and can use this information, in combination with other information he or she has gathered during the course of the functional capacity evaluation, to determine whether maximal effort has been expended. Alternatively, the information could be utilized by a computer programmed to analyze functional capacity.

Although there have been described particular embodiments of the present invention of a new and useful FUNCTIONAL CAPACITY EVALUATION APPARATUS AND METHOD, it is not intended that such references be construed as limitations upon the scope of this invention except as set forth in the claims.

What is claimed is:

1. An apparatus for testing the lifting ability of an individual comprising:
   a detached object to be lifted in free space a fixed predetermined distance
   A first sensor to determine when the lift has begun;
   A second sensor to determine when the lift has been completed; and
   force sensors for determining the force applied by each of the individual's feet during the lift;
   Means for calculating the velocity and acceleration of the lift, said calculating means connected to said first sensor and said second sensor; and,
   means for recording the average force applied by each of the individual's feet during the lift, said recording means connected to said force sensors.

2. The apparatus as described in claim 1 wherein said first sensor is a transmitted beam photoelectric sensor.

3. The apparatus as described in claim 1 wherein said second sensor is a transmitted beam photoelectric sensor.

4. The apparatus of claim 1 further comprising a rack and at least one shelf selectively placed at predetermined locations on said rack wherein said fixed distance is determined by the selective placement of said shelf at height on said rack, and said first sensor is attached to the base of said rack and said second sensor is attached to said shelf, said object being freely movable along any path between said base and shelf.

5. The apparatus of claim 1 further comprising a rack and at least one shelf selectively placed at predetermined locations on said rack wherein said fixed distance is determined by the selective placement of a lower and a higher shelf on said rack, and said first sensor is attached to said lower shelf, and said second sensor is attached to said higher shelf, said object being freely movable along any path between said lower and higher shelf.

6. The apparatus as described in claim 1 wherein said calculating means comprise a microprocessor control system and operator interface.

7. The apparatus described in claim 1, further comprising force sensors for determining the force applied by each of the individual's feet during the lift and means for recording the average force applied by each of the individual's feet during the duration of the lift, said recording means connected to said sensors.

8. The apparatus as described in claim 1 wherein said calculating means comprise a microprocessor control system and operator interface.

9. The apparatus as described in claim 7 further comprising a data retention means for recording the velocity, acceleration, and average force of multiple lifts.

10. The apparatus as described in claim 1, further comprising force sensors for determining the force applied by each of the individual's hands during the lift, and means for recording the average force applied by each of the individual's hands during the duration of the lift, said recording means connected to said force sensors.

11. The apparatus as described in claim 10 wherein said recording means comprise a microprocessor control system and operator interface.

12. An apparatus for testing the lifting capability of an individual comprising:
   a rack having a plurality of supports for shelves;
   at least one shelf selectively positioned on said rack, detached object to be lifted a fixed distance, said fixed distance determined by the selective placement of said shelves on said rack;
   a first sensor for determining when the lift has begun;
   a second sensor for determining when the lift has been complete;
   force sensors for determining the force applied by each of the individual's hands and feet during the lift;
   means for calculating the velocity and acceleration of the lift said, calculating means connected to said first sensor and said second sensor; and,
   means for recording the average force applied by each of the individual's hands and feet during the lift.

13. The apparatus as described in claim 12 wherein said second sensor is a transmitted beam photoelectric sensor.

14. The apparatus as described in claim 12, wherein said second sensor is a transmitted beam photoelectric sensor.

15. The apparatus as described in claim 12 wherein said calculating means comprise a microprocessor control system and operator interface.

16. The apparatus as described in claim 15 wherein said recording means comprise a microprocessor control system and operator interface.

17. The apparatus as described in claim 15 further comprising a data retention means for recording the velocity, acceleration and the average force of multiple lifts.

18. A method for testing the lifting capacity of an individual comprises the steps of:
   providing a detached object to be lifted a fixed distance;
   providing a first sensor near the location where the lift will begin;
   providing a second sensor near the location where the lift will end;
   providing force sensors to measure the force applied by the hands and feet of the individual;
   directing the individual to lift the object;
   monitoring the output from the first sensor so as to determine when the lift has begun;
   monitoring the output from the second sensor so as to determine when the lift has ended;
   monitoring the output of said force sensors during the duration of the lift'
   determining the total time for the lift
   calculating the velocity and acceleration of the lift from the known time and distance;
   determining the average force applied by each of the individual's hands and feet during the duration of the lift;
   utilizing said velocity and acceleration and force to determine whether the individual expended maximal effort.

19. The method as described in claim 18, wherein the steps of monitoring the output from the first sensor, monitoring the output from the second sensor, determining the total time required, and calculating the velocity and acceleration are carried out using a microprocessor system.

20. The method as described in claim 19, wherein the method further comprises the steps of providing a data retention means and recording the velocity, acceleration, and average force of multiple lifts using said data retention means.

* * * * *